(12) United States Patent
Kühnle et al.

(10) Patent No.: US 6,258,832 B1
(45) Date of Patent: Jul. 10, 2001

(54) METHOD FOR PRODUCING THIAZOLIDINEDIONES, AND NEW THIAZOLIDINEDIONES

(75) Inventors: Hans-Frieder Kühnle, Weinheim; Ernst-Christian Witte, Mannheim; Hans-Peter Wolff, Weinheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/381,247
(22) PCT Filed: Mar. 17, 1998
(86) PCT No.: PCT/EP98/01535
§ 371 Date: Sep. 14, 1999
§ 102(e) Date: Sep. 14, 1999
(87) PCT Pub. No.: WO98/42704
PCT Pub. Date: Oct. 1, 1998

(30) Foreign Application Priority Data

Mar. 20, 1997 (DE) ............................. 197 11 616

(51) Int. Cl.$^7$ ........................ A61K 31/427; C07D 417/14
(52) U.S. Cl. ................................. 514/369; 548/183
(58) Field of Search ........................ 548/183; 514/369

(56) References Cited

U.S. PATENT DOCUMENTS

| 4,703,052 | 10/1987 | Eggler et al. | 514/337 |
|---|---|---|---|
| 5,330,998 | 7/1994 | Clark et al. | 514/369 |
| 5,334,604 | 8/1994 | Goldstein et al. | 514/364 |
| 5,463,070 | 10/1995 | Goldstein et al. | 548/236 |
| 5,599,826 | * 2/1997 | Mertens et al. | 514/364 |

FOREIGN PATENT DOCUMENTS

| 177 353 | 4/1986 | (EP) . |
|---|---|---|
| 207 605 | 1/1987 | (EP) . |
| 299 620 | 1/1989 | (EP) . |
| 306 228 A1 | 3/1989 | (EP) . |
| 332 331 A2 | 9/1989 | (EP) . |
| 454501 | * 10/1991 | (EP) . |
| 559 571 | 9/1993 | (EP) . |
| 332 331 B1 | 2/1994 | (EP) . |
| 306 228 B1 | 11/1999 | (EP) . |
| 89/08652 | 9/1989 | (WO) . |
| WO 89/08651 | 9/1989 | (WO) . |
| 92/03425 | 3/1992 | (WO) . |
| WO 93/13095 | 7/1993 | (WO) . |
| 94/27995 | * 12/1994 | (WO) . |
| 95/18125 | 7/1995 | (WO) . |

OTHER PUBLICATIONS

J. Med. Chem., 39:3897–3907 (1996) Hulin et al.
Cantello et al., J. Med. Chem. 37, 3977 (1994).
Tetrahedron 53, (1997), No. 39, pp. 13285–13294.
Abstract corresponding to WO 95/18125, 1995.

* cited by examiner

Primary Examiner—Laura L. Stockton
(74) Attorney, Agent, or Firm—George W. Johnston; William H. Epstein

(57) ABSTRACT

Improved process of compound of formula III (III)

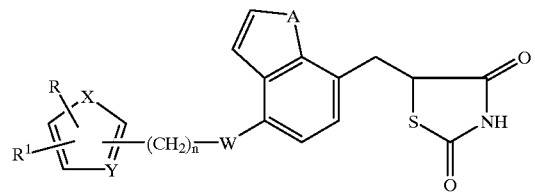

in which
A denotes CH=CH or S
W denotes O
X denotes S, O or NR$^2$ in which the residue R$^2$ is hydrogen or $C_1$–$C_6$ alkyl,
Y denotes CH or N
R denotes naphthyl, thienyl or phenyl which is optionally monosubstituted or disubstituted with $C_1$–$C_3$ alkyl, $CF_3$, $C_1$–$C_3$ alkoxy, F, Cl or bromine,
R$^1$ denotes hydrogen or $C_1$–$C_6$ alkyl and
n denotes 1–3
by reducing a compound of the general formula IV, (IV)

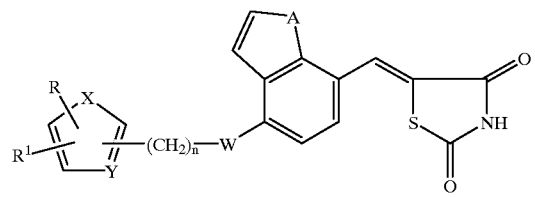

in which A, W, X, Y, R, R$^1$ and n have the meanings stated above
with activated aluminium in a protic solvent,
as well as new compounds of formula III and pharmaceutical preparations containing these compounds.

5 Claims, No Drawings

METHOD FOR PRODUCING THIAZOLIDINEDIONES, AND NEW THIAZOLIDINEDIONES

This application is a 371 of PCT/EP98/01535 filed Mar. 17, 1998.

Thiazolidinedione derivatives of the general formula I are described in the application WO 94/127995,

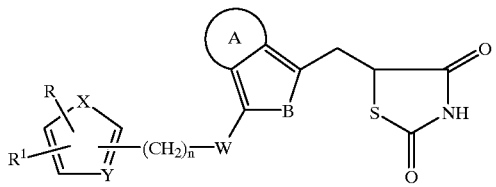

in which
- A represents a carbocyclic ring with 5 or 6 carbon atoms or a heterocyclic ring with a maximum of 4 heteroatoms in which the heteroatoms can be the same or different and denote oxygen, nitrogen or sulphur and the heterocycles can optionally carry an oxygen atom on one or several nitrogen atoms,
- B denotes —CH=CH—, —N=CH—, —CH=N—, O or S,
- W denotes $CH_2$, O, CH(OH), CO or —CH=CH—,
- X denotes S, O or $NR^2$, in which the residue $R^2$ is hydrogen or $C_1$–$C_6$ alkyl,
- Y denotes CH or N
- R denotes naphthyl, pyridyl, furyl, thienyl or phenyl which is optionally monosubstituted or disubstituted with $C_1$–$C_3$ alkyl, $CF_3$, $C_1$–$C_3$ alkoxy, F, Cl or bromine,
- $R^1$ denotes hydrogen or $C_1$–$C_6$ alkyl and
- n denotes 1–3 as well as tautomers, enantiomers, diastereomers and physiologically tolerated salts thereof.

Compounds of the general formula I can form salts with bases since they have an acidic NH group on the thiazolidinedione ring. Suitable pharmaceutical salts are for example alkali salts such as lithium, sodium or potassium salts, alkaline earth salts such as calcium or magnesium salts, other metal salts such as e.g. aluminium salts, ammonium salts or salts with organic bases such as e.g. diethanolamine, ethylenediamine, diisopropylamine and others. The sodium salt is particularly preferred. The salts are for example prepared by treating the compounds of the general formula (I) in a known manner with a stoichiometric amount of the corresponding base.

The compounds are usually produced by a known process via alpha-halogenated carboxylic acids by subsequent synthesis of the thiazolidinedione ring system. In order to produce these carboxylic acids an aromatic amino group is diazotized and the diazonium salt is reacted with ethyl acrylate in the presence of hydrohalic acid and copper salts. This process has some disadvantages for the production of amounts on a multi-kg scale with regard to safety, upscaling, handling and synthesis complexity. For example in the reaction the aromatic amines must be diazotized to form the alpha-halogenated carboxylic acids and reacted with toxic acrylic acid ester and this reaction proceeds with unsatisfactory yields. Furthermore it is extremely problematic to apply this reaction to a larger scale for safety and environmental protection reasons.

A further production process according to the invention comprises the catalytic hydrogenation of compounds of the general formula II,

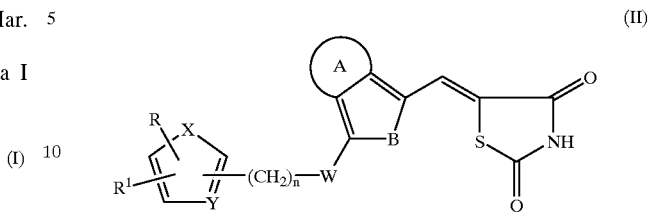

in which A, B, W, X, Y, R, $R^1$ and n have the meanings stated above.

However, the catalytic hydrogenation is very complicated. A poisoning of the catalyst by sulphur may occur especially for types of compound which, in addition to the sulphur contained in the thiazolidine-dione ring, carry a further sulphur atom in the molecule which leads to very long reaction periods and requires a several-fold renewal of the catalyst.

A further process for the reduction of compounds of the general formula II is known from the literature which comprises the use of magnesium as a reducing agent [e.g. C. C. Cantello et al., in J. Med. Chem. 37, 3977 (1994)].

This method circumvents the interference of the catalytic process by sulphur contained in the molecule but in the case of the aforementioned compounds of the general formula II a partial reduction of the five-membered unsaturated heterocycle occurs which leads to impurities of the desired products that are difficult to separate.

Surprisingly it has now been found that compounds of the general formula II can be smoothly reduced with a high purity by the method described last without a partial reduction of the double bonds of the five-membered heterocyclic ring system occurring if metallic aluminium is used instead of magnesium as a reducing agent, the aluminium being advantageously activated by treating the surface with salts of more noble metals.

The process can be applied in particular to a selection of particularly valuable subclasses of the general formula I which are summarized in the following under the general formula III.

Hence a subject matter of the invention is a new process for the production of compounds of the general formula (III)

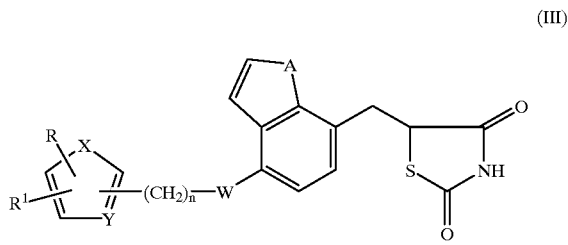

in which
- A denotes CH=CH or S
- W denotes O
- X denotes S, O or $NR^2$ in which the residue $R^2$ is hydrogen or $C_1$–$C_6$ alkyl,
- Y denotes CH or N
- R denotes naphthyl, thienyl or phenyl which is optionally monosubstituted or disubstituted with $C_1$–$C_3$ alkyl, $CF_3$, $C_1$–$C_3$ alkoxy, F, Cl or bromine, $R^1$ denotes hydrogen or $C_1$–$C_6$ alkyl and n denotes 1–3 by reducing a compound of the general formula IV,

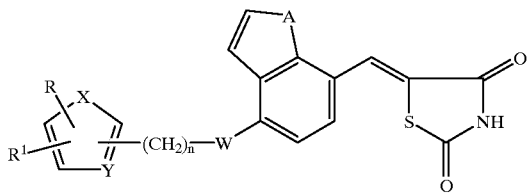

(IV)

in which A, W. X, Y, R, $R^1$ and n have the meanings stated above with activated aluminium in a protic solvent. The surface of the aluminium can be activated by treatment with metal salts that are above aluminium in the electrochemical series. A dilute solution of mercury chloride is particularly suitable. The aluminium can be used in the form of chippings, grit or powder. Lower alcohols, in particular methanol and also water are preferably used as the protic solvent. Aprotic organic solvents that are miscible with alcohols or water can be added to improve the solubility or can be used as the major component. The reaction is carried out at 0–80° C., preferably at room temperature or a slightly increased temperature up to 40° C.

The invention also concerns new compounds of the general formula I which are not described in the application WO 94/27995 and which, in comparison to the compounds described in this application, exhibit a surprisingly better action profile in the treatment of diabetes mellitus. These are the following compounds:

5-{4-[2-(5-methyl-2-(thien-2-yl)-oxazol-4-yl)-ethoxy]-benzo[b]thiophen-7-ylmethyl}-thiazolidine-2,4-dione 5-{4-[2-(5-methyl-2-(4-fluorophenyloxazol)-4-yl)-ethoxy]-benzo[b]thiophen-7-ylmethyl}-thiazolidine-2,4-dione 5-{4-[2-(5-methyl-2-(4-chlorophenyloxazol)-4-yl)-ethoxy]-benzo [b]thiophen-7-ylmethyl}-thiazolidine-2,4-dione 5-{4-[2-(5-methyl-2-(4-trifluoromethylphenyloxazol)-4-yl)-ethoxy]-benzo [b]thiophen-7-ylmethyl}-thiazolidine-2,4-dione 5-{4-[2-(5-methyl-2-(2,4-difluorophenyloxazol)-4-yl)-ethoxy]-benzo [b]thiophen-7-ylmethyl}-thiazolidine-2,4-dione tautomers, enantiomers, diastereomers and physiologically tolerated salts thereof.

The invention in addition concerns pharmaceutical preparations which contain the compounds listed above as an active substance for the treatment of diabetes mellitus. The pharmaceutical preparations are produced and used according to conventional methods described in WO 94/27995.

The following examples are intended to elucidate the new method for the production of compounds of formula (III) without limiting the method to the said special cases. The compounds of the general formula IV are produced according to the process stated in WO 94/27995.

EXAMPLE 1

5-{4-[2-(5-Methyl-2-phenyloxazol-4-yl)-ethoxy]-benzo[b]thiophen-7-ylmethyl}-thiazolidine-2,4-dione a) Production of Activated Aluminium 5 ml of a saturated solution of mercury II chloride in ethanol is diluted to 50 ml with ethanol and briefly shaken with 10 g aluminium needles. Then the solution is decanted and the needles are washed twice with ethanol, once with diethyl ether and once with tetrahydrofuran.

b) Title Compound 10 g activated aluminium needles and 1 ml water are added to a solution of 2.03 g (4.3 mmol) 5-{4-[2-(5-Methyl-2-phenyloxazol-4-yl)-ethoxy]-benzo[b]thiophen-7-ylmethylidene}-thiazolidine-2,4-dione (Fp. 204–207° C.) in 130 ml tetrahydrofuran. Then it is heated for 50 min. while stirring to 50° C. and the solid components are removed by filtration. The filtrate is evaporated and the residue is chromatographed on silica gel with a mixture of 88 parts by volume toluene, 10 parts by volume 2-butanone and 2 parts by volume glacial acetic acid. Yield: 1.65 g (83%), Fp. 204–206° C.

EXAMPLE 2

The following are obtained in an analogous manner:

a) 5-{4-[2-(5-Methyl-2-(thien-2-yl)-oxazol-4-yl)-ethoxy]-benzo[b]thiophen-7-ylmethyl}-thiazolidine-2,4-dione Yield: 57%; Fp.: 115–117° C.
from
  5-{4-[2-(5-Methyl-2-(thien-2-yl)-oxazol-4-yl)-ethoxy]-benzo[b]thiophen-7-ylmethylidene}-thiazolidine-2,4-dione (Fp. 229–234° C.).

b) 5-{4-[2-(5-Methyl-2-phenyloxazol-4-yl)-ethoxy]-naphth-1-ylmethyl}-thiazolidine-2,4-dione Yield: 76%; Fp. 187–191° C.
from
  5-{4-[2-(5-Methyl-2-phenyl-oxazol-4-yl)-ethoxy)]-naphth-1-ylmethylidene}-thiazolidine-2,4-dione (Fp.: 252–254° C.).

c) 5-{4-[2-(5-Methyl-2-(4-fluorophenyloxazol)-4-yl)-ethoxy]-benzo[b]thiophen-7-ylmethyl}-thiazolidine-2,4-dione Yield: 81%, Fp. 205° C.
from
  5-{4-[2-(5-Methyl-2-(4-fluorophenyloxazol)-4-yl)-ethoxy]-benzo[b]thiophen-7-yl-methylidene}-thiazolidine-2,4-dione (Fp. 240° C.).

d) 5-{4-[2-(5-Methyl-2-(4-chlorophenyloxazol)-4-yl)-ethoxy]-benzo[b]thiophen-7ylmethyl}-thiazolidine-2,4-dione Yield: 60%, Fp. 208° C.
from
  5-{4-[2-(5-Methyl-2-(4-chlorophenyloxazol)-4-yl)-ethoxy]-benzo[b]thiophen-7-yl-methylidene}-thiazolidine-2,4-dione (Fp. 270° C.).

e) 5-{4-[2-(5-Methyl-2-(4-trifluoromethylphenyloxazol)-4-yl)-ethoxy]-benzo[b]thiophen-7-ylmethyl}-thiazolidine-2,4-dione Yield: 57%; Fp. 191° C.
from
  5-{4-[2-(5-Methyl-2-(4-trifluoromethylphenyl)-oxazol-4-yl)-ethoxy]-benzo[b]thiophen-7-yl-methylidene}-thiazolidine-2,4 dione (Fp. 260° C.).

f) 5-{4-[2-(5-Methyl-2-(2,4-difluorophenyloxazol)-4-yl)-ethoxy]-benzo[b]thiophen-7-ylmethyl}-thiazolidine-2,4-dione Yield: 78%; Fp. 189° C.
from
5-{4-[2-(5-Methyl-2-(2,4-difluorophenyloxazol)-4-yl)-ethoxy]-benzo[b]thiophen-7-yl-methylidene}-thiazolidine-2,4-dione (amorphous, Fp. from 255° C.).

What is claimed is:

1. A process for the production of compounds of the general formula III

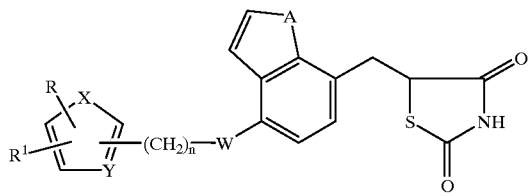

(III)

in which
A denotes CH=CH or S
W denotes O
X denotes S, O or $NR^2$ in which the residue $R^2$ is hydrogen or $C_1$–$C_6$ alkyl,
Y denotes CH or N
R denotes naphthyl, thienyl or phenyl which is optionally monosubstituted or disubstituted with $C_1$–$C_3$ alkyl, $CF_3$, $C_1$–$C_3$ alkoxy, F, Cl or bromine,
$R^1$ denotes hydrogen or $C_1$–$C_6$ alkyl and
n denotes 1–3
wherein a compound of the general formula IV,

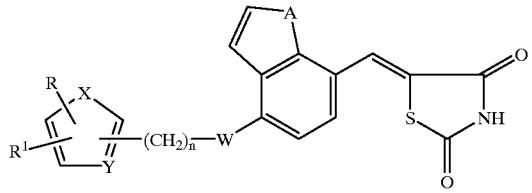

(IV)

in which A, W, X, Y, R, $R^1$ and n have the meanings stated above is reduced with metallic aluminium in a protic solvent.

2. The process as claimed in claim 1, wherein the metallic aluminium used is activated by treatment of the surfaces with salts of noble metals.

3. The process as claimed in claim 2, wherein the aluminium is activated with a mercury chloride solution.

4. A process of claim 1 wherein X denotes O.

5. The process of claim 4 wherein the compound of general formula III is 5-{4-[2-(5-methyl-2-phenyloxazol-4-yl)-ethoxy]-benzo[b]thiophen-7-ylmethyl}-thiazolidine-2,4-dione and the compound of general formula IV is 5-{4-[2-(5-methyl-2-[thien-2-yl)-]phenyloxazol-4-yl)ethoxy]-benzo[b]thiophen-7-ylmethylidene}-thiazolidine-2,4-dione.

* * * * *